|   | United States Patent [19] | [11] | 4,130,719 |
|---|---|---|---|
|   | Cerefice et al. | [45] | Dec. 19, 1978 |

[54] METHOD OF MAKING HIGH PURITY MONOMERS FROM DICARBOXYLIC ACID MONOESTERS AND RESULTANT POLYMERS

[75] Inventors: Steven A. Cerefice, Naperville; Ellis K. Fields, River Forest; Kerford A. Marchant, Jr., Evanston; Edward E. Paschke, Glen Ellyn, all of Ill.

[73] Assignee: Standard Oil Company (Indiana), Chicago, Ill.

[21] Appl. No.: 701,902

[22] Filed: Jul. 1, 1976

[51] Int. Cl.$^2$ ............................................. C07C 69/78
[52] U.S. Cl. ................................... 528/305; 560/66; 560/56; 528/361

[58] Field of Search ...................... 260/473 R, 78.3 R; 560/55, 56, 66

[56] References Cited

PUBLICATIONS

Brindell, G. D. et al., Ind. Eng. Chem. Prod. Res. Dev. 1976, 15(1), 83–88.

*Primary Examiner*—Paul J. Killos
*Attorney, Agent, or Firm*—Gregory E. Croft; Arthur G. Gilkes; William T. McClain

[57] ABSTRACT

High purity monomers, such as methyl p-hydroxymethylbenzoate, are produced by selective reduction of dicaboxylic acid monoesters with diborane. The resultant monomers are suitable for producing new polymers with improved physical properties.

7 Claims, No Drawings

METHOD OF MAKING HIGH PURITY MONOMERS FROM DICARBOXYLIC ACID MONOESTERS AND RESULTANT POLYMERS

BACKGROUND OF THE INVENTION

1. Field of the Invention

This invention primarily relates to a method of making primary alcohol-acid esters from dicarboxylic acid monoesters and polymerizing the primary alcohol-acid esters to form new polymers. More particularly, it relates to the selective reduction of dicarboxylic acid monoesters with diborane to produce monomers of extremely high purity.

2. Description of the Prior Art

Primary alcohol-acid esters, such as methyl p-hydroxymethylbenzoate (Me pHMB), methyl m-hydroxymethylbenzoate (Me mHMB), and methyl 6-hydroxymethyl-2naphthoate are known in the art. Of particular interest has been methyl p-hydroxymethylbenzoate and its corresponding acid, p-hydroxymethylbenzoic acid (pHMBA), which has been synthesized for use as a monomer to make the corresponding homopolymer, poly (p-methylenebenzoate). The acid is believed to have been prepared first as early as 1872 by free-radical bromination of p-toluic acid to p-bromomethyltoluic acid, hydrolysis with aqueous barium hydroxide, and subsequent purification by recrystallization from water. Other methods for the preparation of Me pHMB or pHMBA have been discovered since, including:

(a) Hydrolysis of p-toluic acid and derivatives functionalized at the benzylic position, such as p-halomethylbenzoic acid and esters, p-halomethylbenzonitrile, p-hydroxymethylbenzonitrile; and p-chloromethylbenzoyl chloride.

(b) Oxidation of p-xylene and substituted p-xylenes, such as p-hydroxymethyltoluene, p-acetoxymethyltoluene, and p-xylenediol, and oxidation of p-toluic acid, p-tolualdehyde, and derivatives.

(c) Chloromethylation of benzoic acid and toluene derivatives.

(d) Carboxylation of p-halotoluene compounds via lithium salts.

(e) Disproportionation of terephthaldehyde (Cannizzaro reaction).

(f) Polarographic reduction of dimethyl terephthalate.

A low molecular weight poly (p-methylenebenzoate) has been previously prepared from p-hydroxymethylbenzoic acid and its corresponding methyl and ethyl esters. The polymers thus produced however have been very brittle and are characterized by an inherent viscosity of less than about 0.40 dl/g. (deciliters per gram). As such these polymers are relatively useless. Prior to this invention it has not been known whether the inability to achieve a higher molecular weight (and hence a higher inherent viscosity) has been due to monomer impurity, polyesterification conditions, some intrinsic properties of the monomers to undergo side reactions that limit the degree of polymerization such as ether formation, oxidation, or decomposition, or to some combination of two or more of these factors. Recent work by others confirms that the problem has not been solved. (See Ind. Eng. Chem., Prod. Res. Dev., Vol. 15, No. 1, p. 83 (1976)).

Accordingly, it is an object of this invention to develop a method for making a useful higher molecular weight poly (p-methylenebenzoate) having good impact resistance and characterized by an inherent viscosity greater than about 0.60 dl./g.

It is also an object of this invention to develop a method for producing high purity primary alcohol-acid esters from dicarboxylic acid monoesters.

It is a specific object of this invention to develop a method for producing high purity methyl p-hydroxymethylbenzoate, methyl m-hydroxymethlylbenzoate, and methyl 6-hydroxymethyl-2-naphthoate and polymers therefrom.

These and other objects will become apparent upon further reading of the specification.

SUMMARY OF THE INVENTION

Applicants have discovered a method for making high purity (99.0 + %) primary alcohol-acid esters which enables the production of new polymers and, in the case of poly (p-methylenebenzoate), a higher molecular weight polymer having vastly improved properties over polymers previously known in the art. This particular polymer has excellent impact strength and solvent resistance when made according to this invention and is characterized by an inherent viscosity from 0.6 to 1.5 dl./g. It is particularly useful as an engineering plastic, but can be used in other applications as well.

In one aspect this invention resides in a method of making high purity primary alcohol-acid esters from dicarboxylic acid monoesters comprising the reduction of the dicarboxylic acid monoester with diborane in a non-protic mutual solvent (i.e. both the dicarboxylic acid and diborane are soluble therein) at a temperature from $-20°$ to $+70°$ C. Whereas this method can be used to convert any dicarboxylic acid monoester to its corresponding primary alcohol-acid ester, of particular interest is the exceptional properties exhibited by poly (p-methylenebenzoate) when polymerized from methyl p-hydroxymethylbenzoate produced by this method.

In another aspect the invention resides in a method of producing poly (p-methylenebenzoate) from high purity methyl p-hydroxymethylbenzoate or p-hydroxymethylbenzoic acid comprising (a) formation of a prepolymer by heating the methyl p-hydroxymethylbenzoate or the acid in the presence of a catalyst while distilling off methanol; (b) polycondensation of the prepolymer in the melt at elevated temperatures under vacuum; and (c) polymerizing the polycondensation product in the solid state. The resultant poly (p-methylenebenzoate) has an inherent viscosity of about 0.90 dl/g. and exceptional impact strength. Although either the acid or the ester can be used as the monomer, the ester is preferred because it is the direct product of the diborane reduction reaction, whereas the acid is produced by hydrolysis of the ester. This holds true for the preparation of all the polymers of this invention.

In a further aspect the invention resides in poly (p-methylenebenzoate), as a new composition, having exceptional impact strength and good solvent resistance and characterized by an inherent viscosity from about 0.6 to 1.5 dl./g.

In a still further aspect, the invention resides in the preparation of copolyesters derived from methyl p-hydroxymethylbenzoate, dimethyl terephthalate, and ethylene glycol.

In a still further aspect, the invention resides in other new polymers obtained from polymerization of the pure monomers produced by the aforementioned diborane reduction process such as poly(m-methylenebenzoate), poly(6-methylene-2-naphthoate), and copolymers having a p-methylenebenzoate component and a m-methylenebenzoate component.

DESCRIPTION OF THE PREFERRED EMBODIMENTS

Both aliphatic and aromatic dicarboxylic acid monoesters are selectively reduced to primary alcohol-acid esters in high yields by diborane. Diborane gas can either be used directly or generated in situ or in a separate reactor by addition of boron triflouride etherate, mercurous chloride, or iodine to sodium borohydride in anhydrous tetrahydrofuran or diglyme. Other non-protic solvents in which both diborane and the carboxylic acid are soluble can also be used. An excess of diborane is used conveniently to complete the reaction, which is quantitative at temperatures from $-20°$ to $+70°$ C. The products are isolated by (1) addition of water, which hydrolyzes the intermediate borate esters and excess diborane; (2) extraction into a water immiscible solvent such as benzene, diethyl ether, carbon tetrachloride, chloroform, or dichloromethane; (3) extraction of the organic portion with dilute aqueous sodium bicarbonate, which removes acidic materials; and (4) removal of solvent.

By referring to the following examples, the invention will be described in greater detail.

EXAMPLE 1

Preparation of Methyl p-Hydroxymethylbenzoate (Me pHMB).

To a stirred suspension of monomethylterephthalate (513.0 g., 2.85 moles) and sodium borohydride (94.0 g., 2.47 moles) in 4.0 liters of tetrahydrofuran, was added boron trifluoride etherate (465 g., 3.28 moles) at a rate to maintain a gentle reflux. The mixture was stirred for 2 hours at 20° C. Water (200 ml.) was added slowly, and the solvents were removed on a rotary evaporator. The residue was taken up in 3.5 liters of water and 1.5 liters of dichloromethane, the layers were separated, and the aqueous portion was extracted with dichloromethane (three 400 ml. portions). The combined organic portions were extracted with 2.5% sodium bicarbonate (1.0 liter), then dried over anhydrous sodium sulfate. Removal of solvent in vacuo left 466.5 g. (98.6%) Me pHMB; m.p. 47°–48° C. Distillation at 125°–127° C./0.4 torr and recrystallization from two parts carbon tetrachloride and one-half part hexane at 47° C. gave a purified product: m.p. 48.5°–49.5° C; ir (nujol) 3400–3200, 1725, 1290, 1115, 1050, 1020, and 760 cm.$^{-1}$; nmr (CDCl$_3$) 7.82 and 7.23 (AB quartet, $J_{AB}$=9Hz, 4H), 4.58 (S, 2H), 3.80 (S, 3H), and 3.67 (broad S, 1H); mass spectrum m/e 166 (parent ion), 107 (base peak ion); acetylation gc, 99.91% Me pHMB.

Analysis Calculated for C$_9$H$_{10}$O$_3$: C, 65.1; H, 6.1; Found: C, 65.0; H, 6.2.

EXAMPLE 2

Preparation of p-Hydroxymethylbenzoic Acid (pHMBA).

A mixture of Me pHMB (50.0 g., 0.30 mole) and 200 ml. of water containing sodium hydroxide (13.3 g., 0.33 mole) was refluxed for 3 hours. The colorless solution was filtered from a small amount (0.5 g.) of a gummy solid and extracted with methylene chloride (2 × 50 ml.). The aqueous portion was acidified with concentrated hydrochloric acid to give 37.0 g. of pHMBA: m.p. 180°–181° C. The filtrates were concentrated to 100 ml. at 100° C., cooled to 20° C., and filtered to give 6.7 g. of pHMBA (m.p. 181° C.). The combined yield of pHMBA was 43.7 g. (96%): silylation gc, 99.7% pHMBA.

The crude product was purified by recrystallization from water. After 5.0 g. were dissolved in 75 ml. of water at 100° C., the solution was cooled to 0° C., filtered, washed with cold water, and dried to give 4.85 g. (97% recovery) of pHMBA: m.p. 181°–182° C.; silylation gc, 99.9%, ir (nujol) 3350–3200, 3000–2550, 1690, 1615, 1580, 1425, 1320, 1300, 1180, 1050, 1040, 935, and 760 cm.$^{-1}$; mass spectrum m/e 152 (parent ion), 79 (base peak ion); nmr (D$_2$O/KOD) 7.90 and 7.36 (AB quartet, $J_{AB}$=9Hz, 4H), and 4.60 (S, 2H).

Analysis Calculated for C$_8$H$_8$O$_3$: C, 63.2; H, 5.3 Found: C, 63.0; H, 5.2

EXAMPLE 3

Preparation of Poly (p-Methylenebenzoate) (PpMB).

A prepolymer was prepared by placing 834.0 g. of methyl p-hydroxymethylbenzoate (99.5% pure) into a one liter 3-neck round bottom flask. The flask was equipped with a Teflon stirring paddle, a distilling head, and a thermometer. The flask was heated to 100° C. whereafter 2.5 g. of dibutyl tin maleate catalyst was added. When the contents of the flask reached 150° C. methanol was evolved. Over a 90 minute period, the temperature of the reaction was raised from 150° C. to 250° C. at such a rate as to maintain a moderate distillation of methanol. Vacuum (150 mm. Hg) then was applied for 5 minutes to remove any remaining methanol and the reaction product was poured onto an aluminum pan, cooled, and broken. The inherent viscosity* (I.V.) of the 675.3 g. of white product was 0.16 dl/g.

*Inherent viscosities were determined by dissolving 0.1000 grams of polyester in 25 ml. of 60% phenol: 40% tetrachloroethane by weight. The viscosity was determined at 30° C. using a 1C Ubbelohde viscometer.

Melt polycondensation of the above product (651.4 g.) was carried out in a one liter resin kettle equipped with a stirrer and heated with an oil bath. Polycondensation was conducted for two hours at 272° C. oil bath temperature and 0.22–0.30 mm. Hg vacuum. The inherent viscosity of the resulting light yellow polyester (567.0 g.) was 0.58 dl/g.

A sample of this melt polymer was polymerized in the solid state at 240° C. with a nitrogen sweep for the times shown in Table I. The resultant inherent viscosity, shown in the second column of Table I, reached a value of 0.91 dl/g. after 32 hours of solid state polymerization. Agglomeration was not a problem. For comparison, the first column of Table I shows the inherent viscosities for samples of the prepolymer which were polymerized in the solid state without the intermediate step of melt polycondensation. This solid state polymerization of the prepolymer was carried out at 230°–240° C. and 0.20 mm. Hg vacuum for the times shown in Table I.

TABLE I

Solid State Polymerization of Prepolymer and Melt Polymer

| | Inherent Viscosity (dl/g.) | |
|---|---|---|
| Time (Hours) | Prepolymer | Melt Polymer |
| 0 | 0.16 | 0.58 |
| 4 | — | 0.69 |
| 8 | — | 0.75 |
| 16 | 0.49 | 0.81 |
| 24 | 0.52 | 0.84 |
| 32 | 0.51 | 0.91 |

The physical properties of two different poly (p-methylenebenzoate) injection molded parts are summarized in Table II and compared with data for poly (ethylene terephthalate) and polycarbonate. The two different poly (p-methylenebenzoate) polymers are compared to illustrate the unexpectedly outstanding impact properties of the polymer having the higher inherent viscosity (I.V.). The samples to be molded were vacuum dried at 150° C. overnight and injection molded on an Arburg 220 E/150 machine. The molding conditions were as follows: rear zone temperature, 490° F.; front zone temperature, 530° F.; injection pressure, 13,000 p.s.i.; and mold temperature, 18° F.

TABLE II

Physical Properties of Molded Poly (p-Methylenebenzoate) and Other Polymers

| Physical Property | PpMB | PpMB | PET[1] | PC[2] |
|---|---|---|---|---|
| Initial I.V., dl/g. (before molding) | 0.87 | 0.44 | — | — |
| Part I.V., dl/g. (after molding) | 0.73 | 0.41 | 0.73 | — |
| Tensile Impact, psi. | 231 | 2.3 | 137 | 188 |
| Izod Impact, ft-lb/in. | No break | 0.23 | 0.58 | 15 |
| Heat Deflection Temperature, ° F, 66 psi. | 186 | — | 160 | 278 |
| Yield Tensile Strength, psi. | 7800 | 6120 | 8200 | 9100 |
| Elongation at Yield, % | 7.3 | 7.8 | 6.7 | 11 |
| Ultimate Tensile Strength, psi. | 6320 | — | 5270 | 9430 |
| Elongation at Break, % | 120 | 169 | 410 | 110 |
| Flexural Modulus, psi. | 301,000 | 267,000 | 331,000 | 345,000 |
| Density, g./in.$^3$ | 1.28 | — | 1.34 | 1.21 |
| Hardness, Rockwell R | 113 | — | 127 | 115 |
| Glass Transition Temperature, ° C. | 94 | — | 74 | 145 |
| Melting Point, ° C. | 257 | — | 265 | 260–270 |

[1]Poly(ethylene terephthalate)
[2]Polycarbonate, Lexan 110.

In Table III the solvent resistance of poly (p-methylenebenzoate) having a high inherent viscosity (0.73) is compared with the solvent resistance of polycarbonate and the solvent resistance of poly (p-methylenebenzoate) having a low inherent viscosity (0.41).

TABLE II

Solvent Resistance of Poly (p-Methylenebenzoate) Compared to Polycarbonate (PC)

Observed Effect

| | 5 Minutes | | | 64 Hours | | |
|---|---|---|---|---|---|---|
| Solvent | PC | PpMB (I.V. = 0.41) | PpMB (I.V. = 0.73) | PC | PpMB (I.V. = 0.41) | PpMB (I.V. = 0.73) |
| Benzene | Soften | None | None | Dissolve | Slight Craze | None |
| Toluene | Soften | None | None | Dissolve | Slight Craze | None |
| Methyl ethyl ketone | Craze | Slight Craze | None | Dissolve | Craze | Slight Craze |
| Chloroform | Dissolve | Craze | Craze | Dissolve | Crumbled | Craze |
| Methanol | None | None | None | None | None | None |
| Hexane | None | None | None | None | None | None |

EXAMPLE 4

Preparation of Copolyesters.

By similar methods to those previously described for preparing PpMB, copolyesters from dimethyl terephthalate, ethylene glycol, and methyl p-hydroxymethylbenzoate were synthesized. The results are summarized in Table IV.

TABLE IV

Copolyesters from Methyl p-Hydroxymethylbenzoate (Me pHMB), Dimethyl Terephthalate (DMT) and Ethylene Glycol (EG)

| Mole Ratio | | Tg (° C) | I.V. (dl/g.) |
|---|---|---|---|
| DMT + EG | Me pHMB | | |
| 100 | 0 | 74 | 0.60 |
| 75 | 25 | 81.3 | 0.55 |
| 50 | 50 | 83.3 | 0.51 |
| 25 | 75 | 89.4 | 0.88 |
| 0 | 100 | 94.0 | 0.87 |

Because of the high impact properties contributed by PpMB, these copolymers of PpMB and PET are useful in applications where PET is used, but where higher impact strength is needed. Depending upon the specific properties desired, the copolyester can have from 1 to 99 weight percent of an ethyleneterephthalate component and correspondingly from 99 to 1 weight percent of a p-methylenebenzoate component.

EXAMPLE 5

Preparation of Methyl m-Hydroxymethylbenzoate (Me mHMB).

To a stirred suspension of 21.0 g. of monomethylisophthalate (97% pure, 114 millimoles) and sodium borohydride (4.0 g., 105 millimoles) in tetrahydrofuran (120 ml.), boron trifluoride etherate (20.0 g., 140 millimoles) was added at rate to maintain gentle reflux. The mixture was stirred at room temperature for 4 hours. Water (25 ml.) was added and the solvents were removed on a rotary evaporator. The residue was taken up in water (100 ml.) and extracted with dichloromethane (four 50 ml. portions). The combined organic layer was extracted with 5% sodium bicarbonate (100 ml.), water (100 ml.), and dried. Removal of solvent in vacuo left 18.75 g. (97% yield) of a clear colorless oil; acetylation gc, Me mHMB (99.1%), m-xylenediol (0.26%), high-boilers (0.05%). Fractional distillation gave 90% yield of a center-cut fraction: b.p. 123° C./1.0 torr; acetylation gc, Me mHMB (99.80%), m-xylenediol (0.11%), methyl 3-carboxybenzaldehyde (0.06%), and high-boilers (0.03%); ir (neat) 3425, 1725, 1712 (shoulder), 1455, 1440, 1300, 1210, 1115, and 755 cm.$^{-1}$; nmr (CCl$_4$) 8.0–7.0 (m, 2H), 7.6–7.2 (m, 2H), 4.52 (m, 2H), 4.46 (m, 1H), and 3.80 (s, 3H); mass spectrum m/e 166 (parent ion), 135 (base peak).

Analysis Calculated for C$_9$H$_{10}$O$_3$: C, 65.0; H, 6.1. Found: C, 64.8; H, 6.0.

EXAMPLE 6

Preparation of m-Hydroxymethylbenzoic Acid (mHMBA).

A mixture of 16.1 g. of Me mHMB (95% pure, containing about 5% m-xylenediol), 4.0 g. of sodium hydroxide, and 100 ml. of water was heated at 100° C. for 4 hours. The cooled cloudy solution was extracted with chloroform (two 50 ml. portions) to remove base-insoluble organic compounds. The aqueous portion was acidified and cooled to 0° C. The solids were filtered to give 12.0 g. (86% yield) of mHMBA: m.p. 113°–114° C. Recrystallization from hot water (50 ml.) gave 10.2 g. of 99.6% pure mHMBA: m.p. 116°–117° C.; ir (nujol) 3250, 3100–2550, 1680, 1610, 1590, 1300, 1210, 1060, and 745 cm. $^{-1}$; nmr (acetone-$d_6$ plus a drop of trifluoroacetic acid) 9.6 (s, 2H), 8.1–7.9 (m, 2H), 7.7–7.3 (m, 2H), and 4.78 (s, 2H); mass spectrum m/e 152 (parent ion), 79 (base peak).

Analysis Calculated for $C_8H_8O_3$: C, 63.2; H, 5.3. Found: C, 63.2; H, 5.4.

EXAMPLE 7

Preparation of Poly (m-Methylenebenzoate) (PmMB).

A prepolymer was prepared by placing 123.0 g. of methyl m-hydroxymethylbenzoate into a 300 ml. 3-neck round bottom flask. The flask was equipped with a Teflon stirring paddle, a distilling head, and a thermometer. The flask was heated to 53° C. whereafter 0.3 g. of dibutyl tin maleate catalyst was added. When the contents of the flask reached 145° C., methanol was evolved. Over a 116 minute period, the temperature of the reaction was raised from 145° C. to 250° C. at such a rate as to maintain a moderate distillation of methanol. Vacuum (10 mm. Hg) was then applied for 25 minutes to remove any remaining methanol and the reaction product was poured onto an aluminum pan, cooled, and broken. The inherent viscosity of the 95.3 g. of colorless, transparent product was 0.12 dl/g.

Melt polycondensation of the above product (95.3 g.) was carried out in a polymerization vessel equipped with a stirrer and heated with an oil bath. Polycondensation was conducted for 274 minutes at 480° F. melt temperature and 0.50 mm. Hg vacuum. Fibers could be pulled from the resulting melt. The inherent viscosity of the resulting light amber, transparent polyester (71.9 g.) was 0.44 dl./g. The glass transition temperature was 64° C.

Copolymers containing from 1 to 99 weight parts of a p-methylenebenzoate component and from 99 to 1 weight parts of a m-methylenebenzoate component can similarly be prepared by substituting methyl p-hydroxymethylbenzoate for a portion of the methyl m-hydroxymethylbenzoate when making the prepolymer.

EXAMPLE 8

Preparation of Methyl 6-Hydroxymethyl-2-Naphthoate

To a stirred suspension of monomethyl 2,6-naphthalenedicarboxylate (6.96 g., 30 millimoles) and sodium borohydride (1.03 g., 27 millimoles) in 125 ml. of tetrahydrofuran, boron trifluoride etherate (5.12 g., 36 millimoles) in 25 ml. of tetrahydrofuran was added. The mixture was stirred at room temperature for 2 days. Water (15 ml.) was added and the solvents were removed on a rotary evaporator at reduced pressure. The residue was taken up in water (100 ml.) and extracted with chloroform (four 50 ml. portions). The combined organic layer was extracted with 5% sodium bicaronate (50 ml.), water (50 ml.), and dried. Removal of solvent in vacuo left 6.64 g. (101%) of 99.0% methyl 6-hydroxymethyl-2-naphthoate (by silylation gc). Recrystallation from hot benzene-hexane (6.0 g./100 ml. of 4:1 benzene-hexane) gave 6.25 g. (95%) of purified product: m.p. 120°–121° C.; silylation gc, methyl 6-hydroxymethyl-2-naphthoate (99.5%); ir(nujol) 3270, 1720, 1290, 1200, 1125, 1110, and 815 cm.$^{-1}$; nmr(acetone-$d_6$) 8.46 (s, 1H), 7.90 (m, 4H), 7.48 (m, 1H), 4.78 (s,2H), 4.40 (s, 1H), and 3.90 (s, 3H).

Analysis Calculated for $C_{13}H_{12}O_3$: C, 72.2; H, 5.6. Found: C, 72.2; H, 5.5.

EXAMPLE 9

Preparation of 6-Hydroxymethyl-2-Naphthoic Acid.

A mixture of 12.0 g. of crude methyl 6-hydroxymethyl-2-naphthoate (containing unknown amounts of dimethyl 2,6-naphthalenedicarboxylate, 2,6-naphthalenedicarboxylic acid, and 2,6-bis(hydroxymethyl) naphthalene) sodium hydroxide (2.6 g.), and water (150 ml.) was heated at 100° C. for 1 hour. The solution was filtered hot and neutralized with concentrated hydrochloric acid. The mixture was cooled to 20° C. and the precipitated acid was filtered, washed with water, and dried in a vacuum oven at 85° C. A yield of 10.6 g. (95%) was obtained: m.p. 247°–354° C.; silylation gc, 6-hydroxy-methyl-2-naphthoic acid (80.9%), 2,6-naphthalenedicarboxylic acid (16.5%), other impurities (3.5%). The product was purified by recrystallization of its sodium salt from water. The crude product (7.87 g.) was dissolved in water (120 ml.) at 100° C. containing 1.9 g. of sodium hydroxide. The solution was cooled to 0° C. and the precipitated salt was filtered, washed with cold water (10 ml.), and redissolved in hot water (120 ml.). Acidification with dilute hydrochloric acid gave 5.86 g. (75%) of purified 6-hydroxymethyl-2-naphthoic acid: m.p. 234°–240° C.; silylation gc, 6-hydroxymethyl-2-naphthoic acid (99.3%), 2,6-naphthalene dicarboxylic acid (0.05%), 2,6-bis(hydroxymethyl) naphthalene (0.65%); ir(njuol) 3375, 1680, 1425, 1300, 1190, 1135, 1035, 925, 840, 825, 780, 730, and 675 cm.$^{-1}$; nmr (DMSO-$d_6$) 8.56 (m, 1H), 8.5–7.6 (m, 6H), 7.48 (m, 1H), and 4.65 (s, 2H).

Analysis Calculated for $C_{12}H_{10}O_3$: C, 71.3; H, 5.0. Found: C, 71.3; H, 5.0.

6-Hydroxymethyl-2-naphthoic acid was further purified by recrystallization from ethyl acetate (0.67 g./100 ml. at 77° C.) in 90% recovered yield: m.p. 238°–239° C.; silylation gc, 6-hydroxymethyl-2-naphthoic acid (99.85%).

EXAMPLE 10

Preparation of Poly (6-Methylene-2-Naphthoate).

A prepolymer was prepared by placing 613.2 g. of methyl 6-hydroxymethyl 2-naphthoate into a two liter 3-neck round bottom flask. The flask was equipped with a Teflon stirring paddle, a distilling head, and a thermometer. The flask was heated to 151° C. whereafter 1.85 g. of dibutyl tin maleate catalyst was added. When the contents of the flask reached 161° C. methanol was evolved. Over a 92 minute period, the temperature of the reaction was raised from 161° C. to 234° C. at such a rate as to maintain a moderate distillation of methanol. Vacuum (0.3 mm. Hg) was then applied for 17 minutes to remove any remaining methanol and the reaction product was poured onto an aluminum pan, cooled, and broken. The inherent viscosity (I.V.) of the 527.1 g. of white product could not be determined due to insufficient solubility.

Melt polycondensation of the above product (514.0 g.) was carried out in a one liter resin kettle equipped with a stirrer and heated with an oil bath. Polycondensation was conducted for two hours at 320°–323° C. oil bath temperature and 1.0–2.0 mm. Hg vacuum, producing 448.0 g. of a light yellow polyester.

The melt polycondensation product was then polymerized in the solid state at 240° C. with a nitrogen sweep for 40 hours. The resulting polymer had a glass transition temperature of 136° C. and a melting point of 295° C. Melt flow data showed that the polyester was thermoplastic, but the inherent viscosity could not be determined due to insufficient solubility. The insolubility of this polyester provides utility for many applications where solvent resistance is a primary consideration, such as solvent transport, pipe liners, etc. The insolubility of the polyester is illustrated in TABLE V, wherein 0.1 g. of polyester was placed in 25 ml. of the indicated solvent and heated for 1 hour.

TABLE V

| Insolubility of poly(6-methylene-2-naphthoate) | | |
|---|---|---|
| Solvent | Temperature | Effect |
| Trifluoroethanoic Acid | Reflux | Insoluble |
| 60/40 Phenol/Trichloroethane | 135° C. | Insoluble |
| m-Cresol | Reflux | Insoluble |
| Nitrobenzene | 200° C. | Insoluble |
| Benzophenone | 200° C. | Insoluble |
| Phenyl Ether | 200° C. | Insoluble |
| Hexamethylphosphoramide | 200° C. | Insoluble |
| Decahydronaphthalene | Reflux | Insoluble |

TABLE V-continued

| Insolubility of poly(6-methylene-2-naphthoate) | | |
|---|---|---|
| Solvent | Temperature | Effect |
| Dichlorobenzene | Reflux | Insoluble |
| N-methylpyrrolidone | 200° C. | Insoluble |
| N-methylpyrrolidone (with 1.25 g. LiCl) | 200° C. | Insoluble |
| Sulfuric Acid (Conc.) | 200° C. | Insoluble |
| 1,4-Diphenylbenzene | 230° C. | Insoluble |
| 1,4-Diphenylbenzene | 305° C. | Melted and formed oil on surface |

It will be obvious to those skilled in the art that many variations from the specific example, set forth for purposes of illustration, can be made without departing from the scope of this invention.

What is claimed is:

1. As a composition of matter, poly (m-methylenebenzoate) characterized by an inherent viscosity of at least about 0.44 dl./g.

2. As a composition of matter, poly (6-methylene-2-naphthoate).

3. As a composition of matter, a resinous polymer containing (p-methylenebenzoate) units characterized by an inherent viscosity from about 0.6 to 1.5 dl./g. as determined in a solvent containing 60 percent phenol and 40 percent tetrachloroethane by weight, said polymer exhibiting high impact strength.

4. The composition of claim 3 wherein the polymer is a homopolymer.

5. The composition of claim 4 wherein the polymer is characterized by an inherent viscosity of from about 0.6 to about 0.9 dl./g.

6. The composition of claim 3 wherein the polymer is a copolymer containing (ethylene terephthalate) units.

7. The composition of claim 3 wherein the polymer is a copolymer containing (m-methylenebenzoate) units.

* * * * *

UNITED STATES PATENT OFFICE
CERTIFICATE OF CORRECTION

Patent No. 4,130,719          Dated December 19, 1978

Inventor(s)     Cerefice et al.

It is certified that error appears in the above-identified patent and that said Letters Patent are hereby corrected as shown below:

Abstract, Line 3    "dicaboxylic" should read   --dicarboxylic--

Column 1, line 19    "hydroxymethyl-2naphthoate" should read
                                     --hydroxymethyl-2-naphthoate--

Column 4, line 8    "99.9%,ir" should read   --99.9%; ir--

Column 5, line 38    "TABLE II" should read   --TABLE III--

Column 8, line 29    "hydroxy-methyl" should read   --hydroxymethyl--

Signed and Sealed this

Third Day of July 1979

[SEAL]

Attest:

LUTRELLE F. PARKER

*Attesting Officer*     *Acting Commissioner of Patents and Trademarks*